United States Patent [19]

Hubele

[11] 4,046,911
[45] Sept. 6, 1977

[54] N-(SUBSTITUTED PHENYL)-N-FURANOYL-ALANINE METHYL ESTERS AND THEIR USE IN FUNGICIDAL COMPOSITION AND METHODS

[75] Inventor: Adolf Hubele, Magden, Switzerland

[73] Assignee: Ciba-Geigy Corporation, Ardsley, N.Y.

[21] Appl. No.: 703,037

[22] Filed: July 6, 1976

Related U.S. Application Data

[63] Continuation of Ser. No. 563,036, March 28, 1975, abandoned.

[30] Foreign Application Priority Data

Apr. 2, 1974  Switzerland ............... 4572/74
Feb. 10, 1975  Switzerland ............... 1591/75

[51] Int. Cl.² .................. A01N 9/20; C07D 307/68
[52] U.S. Cl. .................. 424/285; 260/347.4
[58] Field of Search ............... 260/347.4, 347.5; 424/285

[56] References Cited

U.S. PATENT DOCUMENTS 3,598,859  8/1971  Yates et al. ............ 260/471
3,778,512  12/1973  Klenzer et al. ............ 424/285

FOREIGN PATENT DOCUMENTS 2,006,471  8/1970  Germany

*Primary Examiner*—Henry R. Jiles
*Assistant Examiner*—Bernard Dentz
*Attorney, Agent, or Firm*—Harry Falber

[57] ABSTRACT

A microbicidal composition which contains as active substance a compound of the formula I

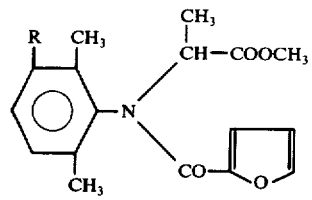

wherein R represents hydrogen or methyl, together with suitable carriers and/or additives which promote the application.

9 Claims, No Drawings

N-(SUBSTITUTED PHENYL)-N-FURANOYL-ALANINE METHYL ESTERS AND THEIR USE IN FUNGICIDAL COMPOSITION AND METHODS

This is a continuation of application Ser. No. 563,036 filed on Mar. 28, 1975, now abandoned.

The present invention provides compounds of the formula I

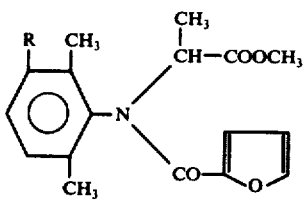

wherein R represents hydrogen or methyl, a process for the manufacture of these compounds, also microbicidal compositions which contain these compounds as active substance, as well as a method of using these compounds as microbicides, preferably for combating phytopathogenic fungi.

Bacterial diseases and mycoses in useful plants are helped by two factors. On the one hand, in plant hybridizing it is a primary objective to attain an increase in yield and an improvement in quality. But in this process the plants frequently lose some of their natural resistance to parasites. On the other hand, experience has shown that bacteria and harmful fungi have developed over the years a substantial resistance to the known pesticides. There is therefore an urgent need for microbicides that are compatible with the cultivated plants and destroy their direct parasites.

Cultivated plants within the scope of the present invention are, for example, cereals, maize, rice, vegetables, sugar beet, soya, ground nuts, fruit trees, ornamental plants, but principally vines, hops, cucumber plants (cucumbers, marrows, melons), solanaceae, such as potatoes, tobacco and tomatoes, as well as bananas, cocoa and rubber plants.

The present invention is based on the surprising observation that it is possible to inhibit or destroy with the compounds of the formula I the fungi which occur on plants or parts of plants (fruit blossoms, leaves, stems, tubers, roots) of these and related cultures or useful plants and also to protect from such fungi which grow later. The active substances are effective against phytophathogenic fungi which belong to the following classes: ascomycetes (e.g. erysiphacea); basidiomycetes, above all rust fungi; fungi imperfecti; but especially against oomycetes which belong to the class of phycomycetes, e.g. phytophthora, peronospora, pseudoperonospora, pythium or plasmopara. In addition, the compounds of the formula I have a systemic action. They can also be used as seed-dressing agents for protecting seeds (fruit, tubers, kernels) and plant cuttings from fungus infections as well as from phytopathogenic fungi which occur in the soil.

The N-(substituted phenyl)-N-furanoyl-anilininemethyl esters of the formula I constitute a hitherto unknown class of new microbicidal active substances which are markedly superior in their field of use to the conventional commercial preparations.

Compounds of the formula I are manufactured by a method according to the invention, for example by acylation of a compound of the formula II

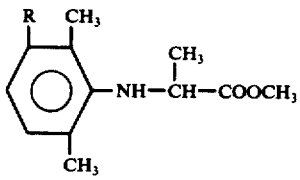

with furan-(2)-carboxylic acid, the acid halide, acid anhydride or ester thereof, in isolated instances also with a furan-(2)-carboxy amide (transamidation).

By another method according to the invention it is also possible to manufacture the compounds of the formula I by converting the acyl anilide of the formula III

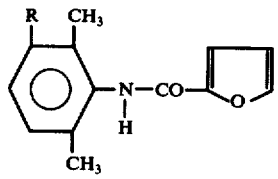

with butyl lithium or sodium hydride into the corresponding alkali salt, which is then reacted with the α-halogenopropionic acid methyl ester to give the desired end product, or else to react the anilide of the formula III with the α-halogenopropionic acid methyl ester in the presence of an alkali carbonate, e.g. $K_2CO_3$, as proton acceptor, preferably with the addition of catalytic amounts of an alkali iodide, e.g. potassium iodide.

In the formulae II and III, R represents hydrogen or methyl, the term "acid halide" denotes preferably acid chloride or acid bromide and the halogen atom in α-halogenopropionic acid methyl ester is preferably chlorine or bromine. The reactions can be carried out in the presence or absence of solvents or diluents which are inert to the reactants. Examples of suitable solvents or diluents are: aliphatic or aromatic hydrocarbons, e.g. benzene, toluene, xylene, petroleum ether; halogenated hydrocarbons, e.g. chlorobenzene, methylene chloride, ethylene chloride, chloroform; ethers and ethereal compounds, e.g. dialkyl ethers, dioxan, tetrahydrofuran; nitriles, e.g. acetonitrile; N,N-dialkylated amides, e.g. dimethyl formamide; anhydrous acetic acid, dimethyl sulphoxide, ketones, e.g. methyl ethyl ketone, and mixtures of such solvents.

The reaction temperatures are between 0° and 180° C, preferably between 20° C and 120° C. It is often advantageous to use acid acceptors or condensation agents. Suitable examples are: tertiary amines, e.g. trialkylamines (e.g. triethylamines), pyridine and pyridine bases, or inorganic bases, e.g. the oxides and hydroxides, hydrogen carbonates and carbonates of alkali metals and alkaline earth metals, as well as sodium acetate. In the above first manufacturing method it is also possible to use a surplus of the respective aniline derivative of the formula II as acid acceptor.

The process of manufacture which proceeds from compounds of the formula II can also be carried out without acid acceptors; in some instances it is expedient to pass in nitrogen in order to expel the hydrogen halide that has formed. In other instances it is very advantageous to use dimethyl formamide as reaction catalyst.

Particulars on the manufacture of the intermediates of the formula II can be inferred from the methods which are generally indicated for the manufacture of anilinealkane acid esters in the following publications:

J. Org. Chem. 30, 4101 (1965); Tetrahedron 1967, 487; Tetrahedron 1967, 493.

The compounds of the formula I contain an asymmetrical carbon atom in the propionic acid ester chain and can be resolved into the optical antipodes in the customary manner. In this connection, the enantiomeric D-form has the more pronounced microbicidal action.

Within the scope of the invention, those compounds, their compositions and their use which refer to the D-configuration of the formula I are accordingly preferred. These D-forms have in ethanol or acetone a negative angle of rotation.

The pure, optical D-antipodes are manufactured, for example, by preparing the racemic compound of the formula IV

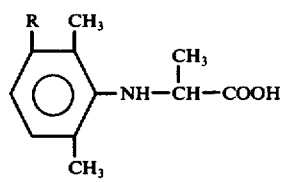

(R=H or CH₃)

and then reacting this in known manner with a nitrogen-containing, optically active base to give the corresponding salt. The pure D-form is obtained stepwise by fractional crystallisation of the salt and subsequent liberation of the acid of the formula IV which is enriched with the optical D-antipode and, if appropriate, by repetition (also repetition several times) of the salt formation, crystallisation and liberation of the α-anilinopropionic acid of the formula IV. From this pure D-form it is then possible to obtain the optical D-configuration of the ester of the formula II in conventional manner, for example in the presence of HCl or H₂SO₄, with methanol. A suitable optically active organic base is, for example, α-phenylethyl amine.

Instead of fractional recrystallization, it is also possible to obtain the enantiomeric D-form of the formula IV by replacing the hydroxy group in the naturally occurring L(+) lactic acid by halogen and reacting this product further with 2,6-dimethylaniline or 2,3,6-trimethylaniline with reversal of the configuration.

Besides the optical isomerism, when R = CH₃, there occurs in the furanoylation of the compound II (or in the reaction of the compound III with α-halogenopropionic acid methyl ester) an atropisomerism about the phenyl-N<axis, as a consequence of the steric hindrance of the two radicals additionally introduced at the nitrogen atom of the trimethylaniline. Provided no synthesis is carried out with the aim of isolating pure isomers, compound 2 (the manufacture of which is described hereinafter) occurs in the manufacture as a mixture of 4 isomers. However, the better fungicidal action of the enantiomeric D-form (in comparison to the D,L-form or the L-form) is retained and is not noticeably affected by the atropisomerism.

The manufacture of the active substances of the formula I is illustrated by the following Examples 1 and 2.

EXAMPLE 1

Manufacture of

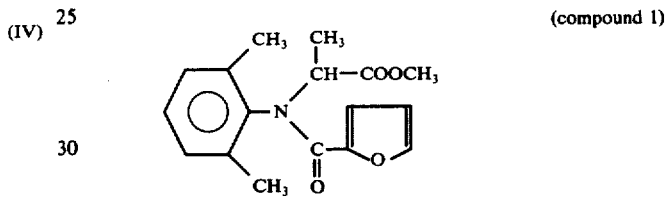

(compound 1)

N-(1'-methoxycarbonylethyl)-N-(furan-(2")-carbonyl)-2,6-dimethylaniline

With stirring, 12.6 g of furan-2-carboxylic acid chloride are added dropwise to 18.2 g of N-(1'-methoxycarbonylethyl)-2,6-dimethylaniline in 10 ml of anhydrous toluene and 0.2 ml of dimethyl formamide. After the weakly exothermic reaction has subsided, the reaction mixture is refluxed for 5 hours and the hydrogen chloride which has formed is completely removed by passing in nitrogen. The solvent is removed and the residue is distilled in vacuo; b.p. 166°–168° C/0.06 Torr. The congealed end product melts between 81°–84° C after recrystallisation from toluene/petroleum ether. X-ray powder patterns show that the product is polymorphous. One of the two modifications melts at 85° C. The enantiomeric D-configuration and its primary products have the following physical data:

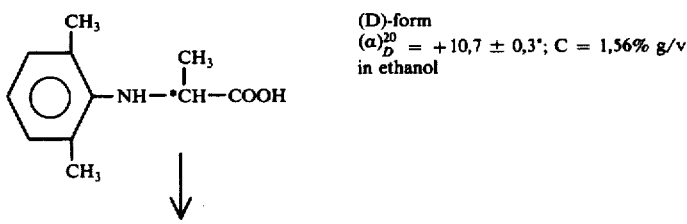

(D)-form
$(\alpha)_D^{20} = +10,7 \pm 0,3°$; C = 1,56% g/v in ethanol

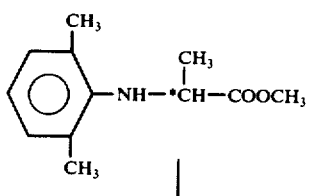

-continued (D)-form
$(\alpha)_D^{20} = +29.8 \pm 0.5°; C = 1.52\%$ g/v
in methanol

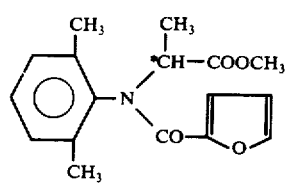

(compound Ia)

(D)-form     m.p. 102 - 103°
$(\alpha)_D^{20} = -47.0 \pm 0.7°$
C = 1.73% g/v in acetone

EXAMPLE 2

Manufacture of

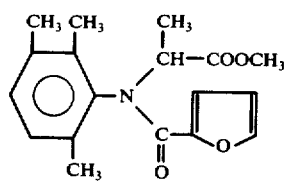

(compound 2)

N(1'-methoxycarbonyl-ethyl)-N-(furan-(2")-carbonyl)-2,3,6-trimethylaniline.

a. A suspension of 51.5 g (0.382 mole) of 2,3,6-trimethylaniline, 35.3 g of NaHCO₃ and 126 ml (1.15 moles) of 2-bromopropionic acid methyl ester is stirred for 6 hours at a bath temperature of 130° C, then cooled, filtered from NaBr-salt and distilled. Yield: 67.3 g of α-(2,3,6-trimethylanilino)propionic acid methyl ester (b.p. 144°-146° C/9 Torr.)

b. A suspension of 33.5 g (0.152 mole) of the ester obtained according to a) and 18 g (0.17 mole) of sodium carbonate in 200 ml of absolute benzene is treated dropwise with 16.7 ml (0.17 mole) of furan-2-carboxylic acid chloride at 60°-70° C and kept thereat for 4 hours. The reaction mixture is cooled and filtered and the filtrate concentrated. The end product crystallises from isopropyl ether (m.p. 98°-102° C).

The D-form of compound 2 is obtained as a mixture of atropisomers (=compound 2a) by acylating the D-form of the α-(2,3,6-trimethylanilino)-propionic acid methyl ester with furan-(2)-carboxylic acid or one of its reactive derivatives. The percentage amount of each of these isomers obtained depends on the respective manufacturing conditions.

The compounds of the formula I can be used with other suitable pesticidal or active substances which promote plant growth in order to improve their activity spectrum.

The compounds of the formula I can be used by themselves or together with suitable carriers and/or other additives. Suitable carriers and additives can be solid or liquid and correspond to the customary substances used in formulation technology, for example natural or regenerated mineral substances, solvents, dispersants, wetting agents, stickers, thickeners, binders or fertilisers. The amount of active substance in commercially useful compositions is between 0.1 and 90%.

The compounds of the formula I can be applied in the following process forms (the percentages by weight in brackets denote advantageous amounts of active substance):

solid forms: dusts and tracking agents (up to 10%); granules, coated granules, impregnated granules and homogeneous granules (1 to 80%);

liquid forms: a) active substance concentrates which are dispersible in water: wettable powders and pastes (25-90% in the commercial pack, 0.01 to 15% in ready for use solution); emulsion concentrates and concentrated solutions (10 to 50%; 0.01 to 15% in ready for use solution); b) solutions (0.1 to 20%).

The active substances of the formula I can be formulated, for example, as follows:

Dusts: The following substances are used to manufacture (a) a 50% and (b) a 2% dust:

a.
5 parts of active substance 2;
95 parts of talcum;

b.
2 parts of active substance 1;
1 part of highly disperse silicic acid,
97 parts of talcum.

The active substances are mixed with the carriers and ground and in this form can be processed to dusts for application.

Granules: The following substances are used to manufacture 5% granules:

5 parts of active substance 1
0.25 parts of epichlorohydrin
0.25 parts of cetyl polyglycol ether
3.50 parts of polyethylene glycol
91 parts of kaolin (particle size 0.3-0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such microgranules are advantageously used for combating soil fungi.

Wettable powders: The following constituents are used to manufacture (a) a 70%, (b) a 40%, (c) and (d) a 25% and (e) a 10% wettable powder:

a.
70 parts of N-(1'-methoxycarbonyl-ethyl)-N-[furan-(2")-carbonyl]-2,6-dimethylaniline (active substance 1 a (D-form) according to the present invention)
5 parts of sodium dibutyl naphthysulphonate
3 parts of naphthalenesulphonic acid/phenolsulphonic acid/formaldehyde condensate (3:2:1)
10 parts of kaolin
12 parts of Champagne chalk.

b.
40 parts of active substance 2
5 parts of the sodium salt of ligninsulphonic acid
1 part of the sodium salt of dibutylnaphthalenesulfonic acid
54 parts of silicic acid.

c.
25 parts of active substance 2a (D-form)
4.5 parts of calcium ligninsulphonate
1.9 parts of a Champagne chalk/hydroxyethyl cellulose mixture (1:1)
1.5 parts of sodium dibutylnaphthalene sulphonate
19.5 parts of silicic acid
19.5 parts of Champagne chalk
28.1 parts of kaolin.

d.
25 parts of active substance 2
2.5 parts of isooctylphenoxy-polyoxyethylene-ethanol
1.7 parts of a Champagne chalkhydroxyethyl cellulose mixture (1:1)
8.3 parts of sodium aluminum silicate
16.3 parts of kieselguhr
46 parts of kaolin.

e.
10 parts of active substance 1a (D-form)
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of every desired concentration and can be used in particular for application to leaves.

Emulsifiable concentrates: The following substances are used to to manufacture a 25% emulsifiable concentrate:
25 parts of active substance 1
2.5 parts of epoxidised vegetable oil
10 parts of an alkylarylsulphonate/fatty alcohol polyglycol ether mixture
5 parts of dimethyl formamide
57.5 parts of xylene.

By diluting such concentration with water it is possible to manufacture emulsions of every desired concentration which are especially suitable for application to leaves.

EXAMPLE 3

Action against Phytophthora infestans on Solanum lycopersicum (tomatoes)

Ia. Residual preventive action

Solanum lycopersicum plants of the "Roter Gnom" variety are infected when 3 weeks old with a zoospore suspension of Phytophthora infestans after they have been sprayed with a broth prepared from the active substance processed to a wettable powder and containing 0.05% of active substance, and dried. They are then kept for 6 days in a climatic chamber at 18° to 20° C and high humidity, which is produced with an artificial wet fog. After this time typical leaf specks appear. Their number and size are the criterion for evaluating the tested substance.

Ib. Curative action

"Rotor Gnom" tomato plants are sprayed when 3 weeks old with a zoospore suspension of the fungus and incubated in a climatic chamber at 18° to 20° C and saturated humidity. The humidifying is interrupted after 24 hours. After the plants have been dried, they are sprayed with a broth which contains the active substance formulated as wettable powder in a concentration of 0.05%. After the spray coating has dried, the plants are again kept in the humid chamber for 4 days. Size and number of the typical leaf specks which have occurred during this time are the criterion for evaluating the effectiveness of the tested substances.

II. Preventative-systemic action

The active substance is applied as wettable powder in a concentration of 0.05% (referred to the volume of the soil) to the surface of the soil of 3 week old "Rotor Gnom" tomatoes in pots. Three days later the underside of the leaves of the plants are sprayed with a zoospore suspension of Phytophthora infestans. The plants are then kept for 5 days in a spray chamber at 18° to 20° C and saturated humidity, after which time typical leaf specks form. The number size of the specks serve the criterion for evaluating the effectiveness of the tested substances.

In these three tests, the compounds of the formula I have a pronounced leaf-fungicidal action, i.e. the fungus infection is below 5%. When the D-forms of the compounds are applied, i.e. active substances 1*a* and 2*a*, the fungus infection is below 5% in all three tests even at rates of application of 0.02%.

EXAMPLE 4

Action against Plasmoporara viticola (Bert. et Curt.) (Berl. et De Toni) on vines a. Residual preventive action Vine cuttings of the variety "Chasselas" were reared in a greenhouse. Three plants in the 10 leaf stage were sprayed with a broth prepared from the active substance and formulated as a wettable powder. After the coating layer had dried, the plants were infected on the underside of the leaves with the spore suspension of the fungus. The plants were subsequently kept for 8 days in a humid chamber, after which time symptoms of the disease were visible on the control plants. The number and size of the infected areas on the tested plants served as criterion for evaluating the effectiveness of the tested active substances.

b. Curative action

Vine cuttings of the variety "Chasselas" were reared in a greenhouse and infected in the 10 leaf stage with a spore suspension of Plasmopara viticola on the underside of the leaves. After they had been kept for 24 hours in a humid chamber, the plants were sprayed with an active substance broth prepared from a wettable powder of the active substance. The plants were then kept for a further 7 days in a humid chamber, after which time the symptoms of the disease were visible on the control plants. The number and size of the infected areas on the treated plants served as criterion for evaluating the effectiveness of the tested substances.

In both these tests of Example 4, the compounds of the formula I exhibit a pronounced fungicidal action in the following concentrations:

| Active Substance | Concentration | Fungus infection in a) and b) |
|---|---|---|
| 1 | 0,05 % | 0 – 5 % |
|  | 0,02 % | 0 – 5 % |
| 1a | 0,02% | 0 – 5 % |
| 2 | 0,05 % | 0 – 5 % |
|  | 0,02 % | 0 – 5 % |
| 2a | 0,02 % | 0 – 5 % |
| Control | — | 100 % |

EXAMPLE 5

Action against Pythium debaryanum in Beta vulgaris (sugar beet)

a. Action after soil application

The fungus is cultivated on sterile oat kernels and added to a mixture of earth and sand. Flower pots are filled with the infected soil in which sugar beet seeds are then sown. Immediately after sowing, the tests preparations formulated as wettable powders are poured in the form of aqueous suspensions over the soil (0.002% active substance referred to the volume of the soil). The pots are then stood for 2–3 weeks in a greenhouse at 20°-24° C. The soil is kept uniformly moist by gently spraying it with water. The emergence of the sugar beet plants as well as the number of healthy and sick plants are ascertained in evaluating the tests.

b. Action after seed treatment application

The fungus is cultivated on sterile cat kernels and added to a mixture of earth and sand. Flower pots are filled with the infected soil and sugar beet seeds which have been treated with the test preparations formulated as seed dressing powders are sown therein (0.1% active substance referred to the weight of the seeds). The pots are then stood in a greenhouse for 2–3 weeks at 20°-24° C. The soil is kept uniformly moist by gently spraying it with water. The emergence of the sugar beet plants as well as the number of healthy and sick plants are ascertained.

Under the conditions of both test (a) and test (b), 85% of the sugar beet plants emerged after treatment with one of the active substances 1, 1a, 2 or 2a and had a healthy appearance. Less than 20% of the untreated control plants emerged and their appearance was in part sickly.

I claim:

1. An anilide of the formula I

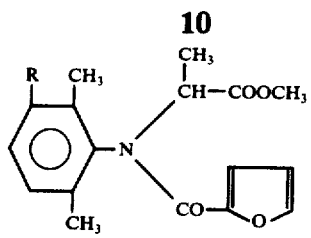

wherein R represents hydrogen or methyl.

2. N-(1'-methoxycarbonyl-ethyl)-N-(furan-(2")-carbonyl)-2,6-dimethylaniline of the formula

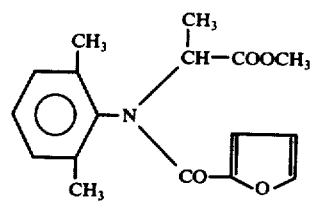

according to claim 1.

3. N-(1'-methoxycarbonyl-ethyl)-N-(furan-(2")-carbonyl)-2,3,6-trimethylaniline.

4. A compound according to claim 1 in the enantiomeric D-configuration.

5. A fungicidal composition which contains as active substance a fungicidally effective amount of a compound of the formula I

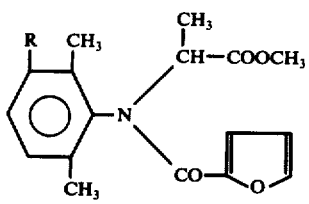

wherein R represents hydrogen or methyl, together with a suitable carrier therefor.

6. A fungicidal composition according to claim 5 which contains as active substance N-(1'-Methoxycarbonyl ethyl)-N-(furan-(2")-carbonyl)-2,6-dimethylaniline.

7. A fungicidal composition according to claim 5 which contains as active substance N-(1'-methoxycarbonyl-ethyl)-N-(furan-(2")-carbonyl)-2,3,6-trimethylaniline.

8. A method of combating phytopathogenic fungi which comprises applying to the locus thereof a fungicidally effective amount of N-(1'-methoxycarbonyl-ethyl)-N-(furan-(2")-carbonyl)-2,6-dimethylaniline.

9. A method of combating phytopathogenic fungi which comprises applying to the locus thereof a fungicidally effective amount of N-(1'-methoxycarbonyl)-ethyl)-N-(furan-(2")-carbonyl)-2,3,6-trimethylaniline.

* * * * *